(12) United States Patent
Bjork et al.

(10) Patent No.: US 7,097,616 B2
(45) Date of Patent: Aug. 29, 2006

(54) SURGICAL CLAMP

(75) Inventors: Todd M. Bjork, River Falls, WI (US); Todd William Sharratt, Birchwood, MN (US); Christopher Lee Berg, Crystal, MN (US)

(73) Assignee: Minnesota Scientific, Inc., White Bear, MN (US)

( * ) Notice: Subject to any disclaimer, the term of this patent is extended or adjusted under 35 U.S.C. 154(b) by 0 days.

(21) Appl. No.: 10/681,480

(22) Filed: Oct. 8, 2003

(65) Prior Publication Data

US 2005/0080321 A1  Apr. 14, 2005

(51) Int. Cl.
 *A61B 1/32* (2006.01)
(52) U.S. Cl. ................................... 600/230
(58) Field of Classification Search ............ 600/227, 600/230, 233, 234; 403/389, 384, 391; 248/291.1, 248/292.12, 231.61; 24/535, 540, 541, 513–515
See application file for complete search history.

(56) References Cited

U.S. PATENT DOCUMENTS

| | | | |
|---|---|---|---|
| 3,384,077 A * | 5/1968 | Gauthier | 600/234 |
| 3,384,078 A * | 5/1968 | Gauthier | 600/215 |
| 3,749,088 A * | 7/1973 | Kohlmann | 600/215 |
| 3,965,890 A * | 6/1976 | Gauthier | 600/215 |
| 4,545,572 A * | 10/1985 | Day | 5/637 |
| 4,718,151 A | 1/1988 | LeVahn et al. | 24/535 |
| 5,020,195 A | 6/1991 | LeVahn | 24/514 |
| 5,242,240 A | 9/1993 | Gorham | 403/391 |
| 5,601,554 A | 2/1997 | Howland et al. | 606/61 |
| 5,727,899 A | 3/1998 | Dobrovolny | 403/389 |
| 5,792,046 A | 8/1998 | Dobrovolny | 600/234 |
| 5,810,817 A * | 9/1998 | Roussouly et al. | 606/61 |
| 6,042,540 A | 3/2000 | Johnston et al. | 600/213 |
| 6,613,049 B1 * | 9/2003 | Winquist et al. | 606/59 |
| 6,616,664 B1 | 9/2003 | Walulik et al. | 606/57 |
| 6,736,775 B1 * | 5/2004 | Phillips | 600/234 |
| 2002/0177754 A1 | 11/2002 | Phillips | 600/234 |
| 2003/0120132 A1 | 6/2003 | Phillips | 600/210 |
| 2003/0191370 A1 | 10/2003 | Phillips | 600/201 |

* cited by examiner

*Primary Examiner*—Eduardo C. Robert
*Assistant Examiner*—Anuradha Ramana
(74) *Attorney, Agent, or Firm*—Westman, Champlin & Kelly, P.A.

(57) ABSTRACT

A surgical joint includes a first clamping member for engaging a first support member and a second clamping member for engaging a second support member. The first clamping member includes a clamping bore wherein the first support member is positionable within the clamping bore. The second clamping member includes a socket wherein the second support member is positionable within the socket. A shaft is disposed through the first clamping member and is in communication with the second clamping member. An actuating mechanism is coupled to the shaft wherein the actuating mechanism is positionable to force the first clamping member frictionally engages the first support member and the second clamping member frictionally engages the second support member.

13 Claims, 11 Drawing Sheets

SURGICAL CLAMP

CROSS-REFERENCE TO RELATED APPLICATION(S)

None.

BACKGROUND OF THE INVENTION

The present invention relates generally to a surgical clamp for use in mounting a retractor support apparatus with respect to an operating table. More particularly, the present invention relates to a clamp that can be positioned about the retractor support apparatus in a selected position.

Prior to performing a surgical procedure requiring retraction, a retractor support apparatus is typically constructed about a surgical site. The retractor support apparatus is attached to a field post that is attached to a surgical table with the field post extending upwardly from the surgical table.

The retractor support apparatus extends over the surgical table and can include as little as one support member or numerous support members. Retractors and other surgical equipment are positioned about the surgical site by being secured with a clamp attached to the retractor support apparatus.

However, the retractor support apparatus can be burdensome and difficult to position. Additionally, the clamp is typically free to move along the length of the field post which creates additional difficulty in securing the retractor support apparatus with the clamp. Therefore, securing the retractor support apparatus with a clamp and positioning the clamp in a selected position on the field post can pose difficulties.

The design of the clamp can also add to the difficulty in mounting the retractor support apparatus to the field post. The retractor clamp typically includes first and second clamping members that are generally in the shape of the letter "U". Clamping members having U-shaped structures are disclosed in U.S. Pat. Nos. 4,718,151, 5,020,195, 5,242,240 and 5,792,046, all of which are assigned to the same assignee as the assignee of the present application. The object to be clamped is placed in a clamping bore defined by the legs of the U-shaped structure where movement of the legs towards each other causes the object to be clamped within the clamping bore.

However, the weight and configuration of the retractor support apparatus may create potential difficulties in positioning the end of the retractor support apparatus within the clamping bore. Additionally, once the end of the retractor support apparatus is positioned within the U-shaped structure, the retractor support apparatus must be slid into a selected position prior to clamping the retractor support apparatus in the selected position.

SUMMARY OF THE INVENTION

The present invention includes a surgical joint having a first-clamping member for engaging a first support member and a second clamping member for engaging a second support member. The first clamping member includes a clamping bore wherein the first support member is positionable within the clamping bore. The second clamping member includes a socket wherein the second support member is positionable within the socket. A shaft is disposed through the first clamping member and is in communication with the second clamping member. An actuating mechanism is coupled to the shaft such that the actuating mechanism is positionable to force the first clamping member to frictionally engage the first support member and the second clamping member to frictionally engage the second support member.

DETAILED DESCRIPTION OF THE PREFERRED EMBODIMENTS

Figure 1:
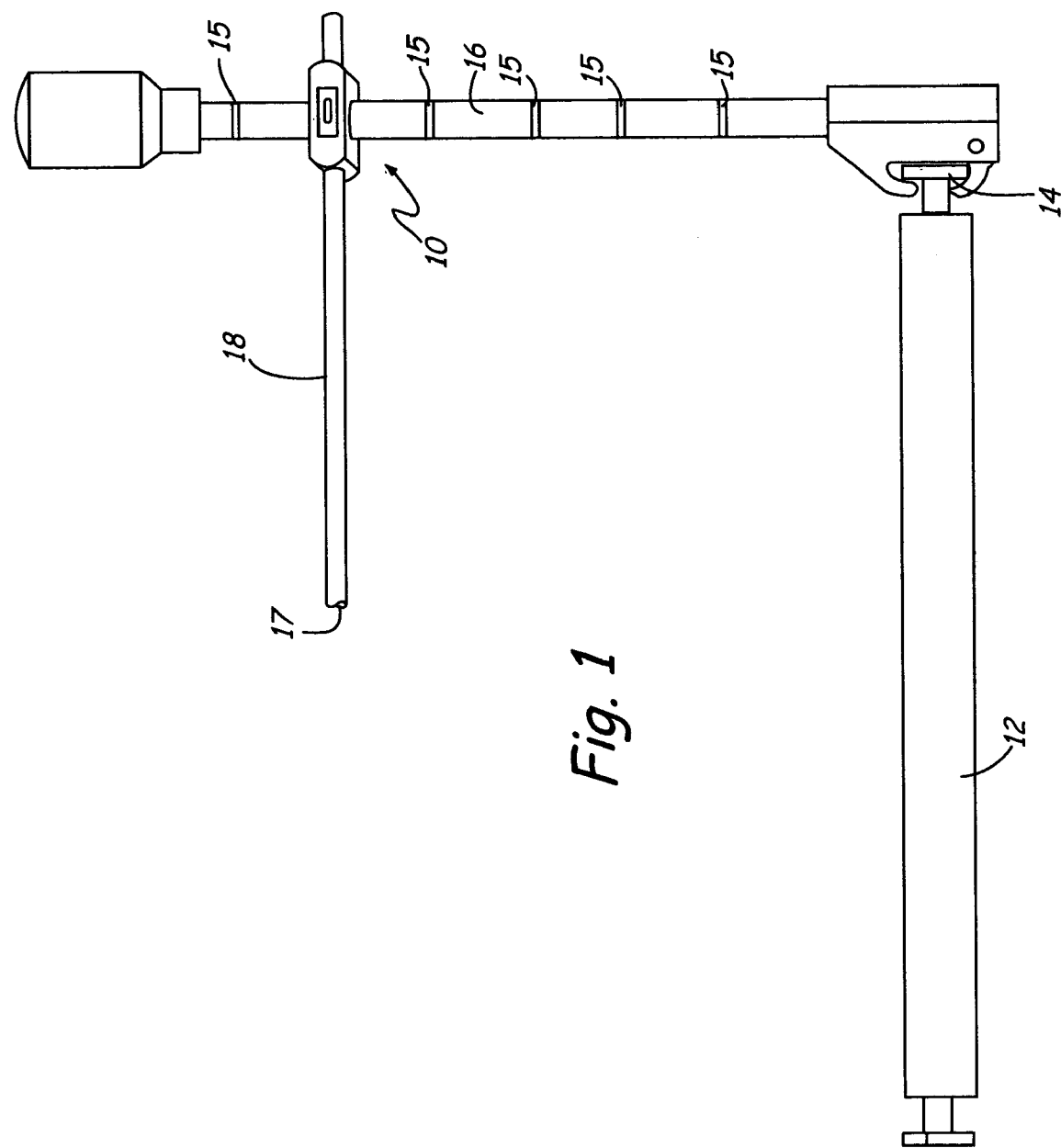
FIG. 1 is a side view of the surgical clamp of the present invention clamping a retractor support apparatus to a field post clamped to a surgical table.

The present invention includes a surgical clamp illustrated in FIG. 1 at 10. The surgical clamp 10 secures a retractor support apparatus 18 to a field post 16 where the field post 16 is mounted to a rail 14 of a surgical table 12.

Figure 2:
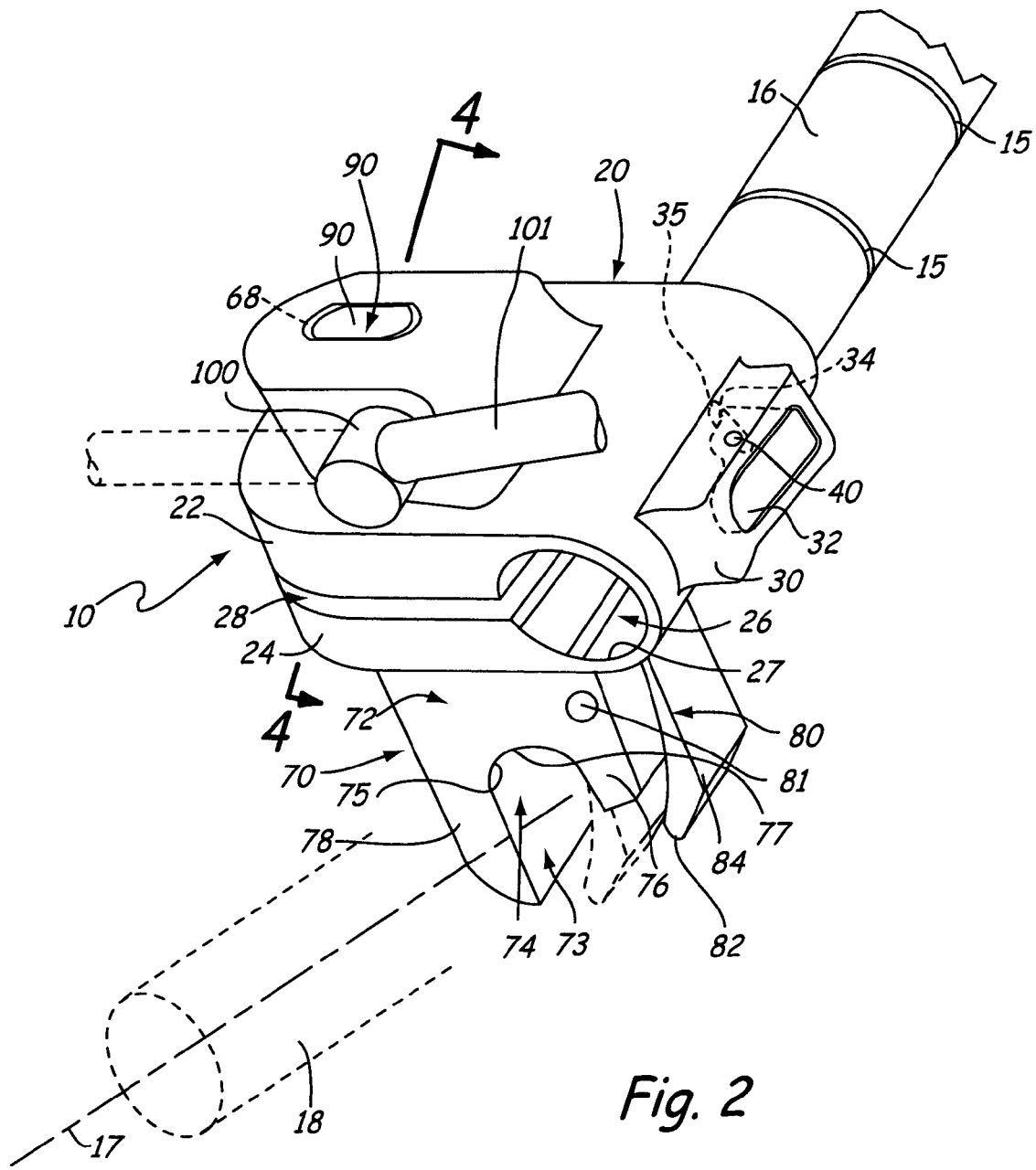
FIG. 2 is a perspective view of the surgical clamp of the present invention.

Referring to FIG. 2, the surgical clamp 10 includes a first clamping member 20 that engages the field post 16 and a second clamping member 70 that engages the retractor support apparatus 18. A shaft 90 is positioned through the first clamping member 20 and engages the second clamping member 70. An actuating mechanism 100 is coupled to the shaft 90 where the actuating mechanism 100 is positionable between a first position and a second position.

In the first position, the first and second clamping members 20, 70, respectively, are in a nonclamping position where the first clamping member 20 is positionable on the field post 16. The retractor support apparatus 18 is positionable within the second clamping member 70 and the second clamping member 70 is rotatable with respect to the first clamping member 20.

In the second position, the first and second clamping members 20, 70, respectively, are positioned into clamping positions. In the clamping position, the first clamping member 20 frictionally engages the field post 16, the second clamping member 70 frictionally engages the retractor support apparatus 18 and the second clamping member 70 is rotatably fixed with respect to the first clamping member 20.

The first clamping member 20 is of a unitary construction having a first resilient leg 22 and a second resilient leg 24 defining a clamping bore 26. A clamping slot 28 separates the first and second resilient legs 22, 24, respectively. The field post 16 is positioned within the clamping bore 26 where the first clamping member 20 is positionable along a length of the field post 16. Although the first clamping member 20 is described as having a unitary construction, a non-unitary construction of the first clamping member 20 is within the scope of the present invention.

A pawl 32 is pivotally attached to a frame 30 extending from the first clamping member 20. A gripping end 34 of the pawl 32 extends into the clamping bore 26 through a pawl passing slot 35 that intersects the clamping bore 26. The gripping end 34 engages one of a plurality of annular grooves 15, preferably uniformly spaced, along a length of the field post 16 to retain the first clamping member 20 on the field post 16 when the clamp 10 is in the non-clamping position. With the gripping end 34 positioned within one of annular grooves 15, the first clamping member 20 is rotatable about the field post 16.

Figure 3:
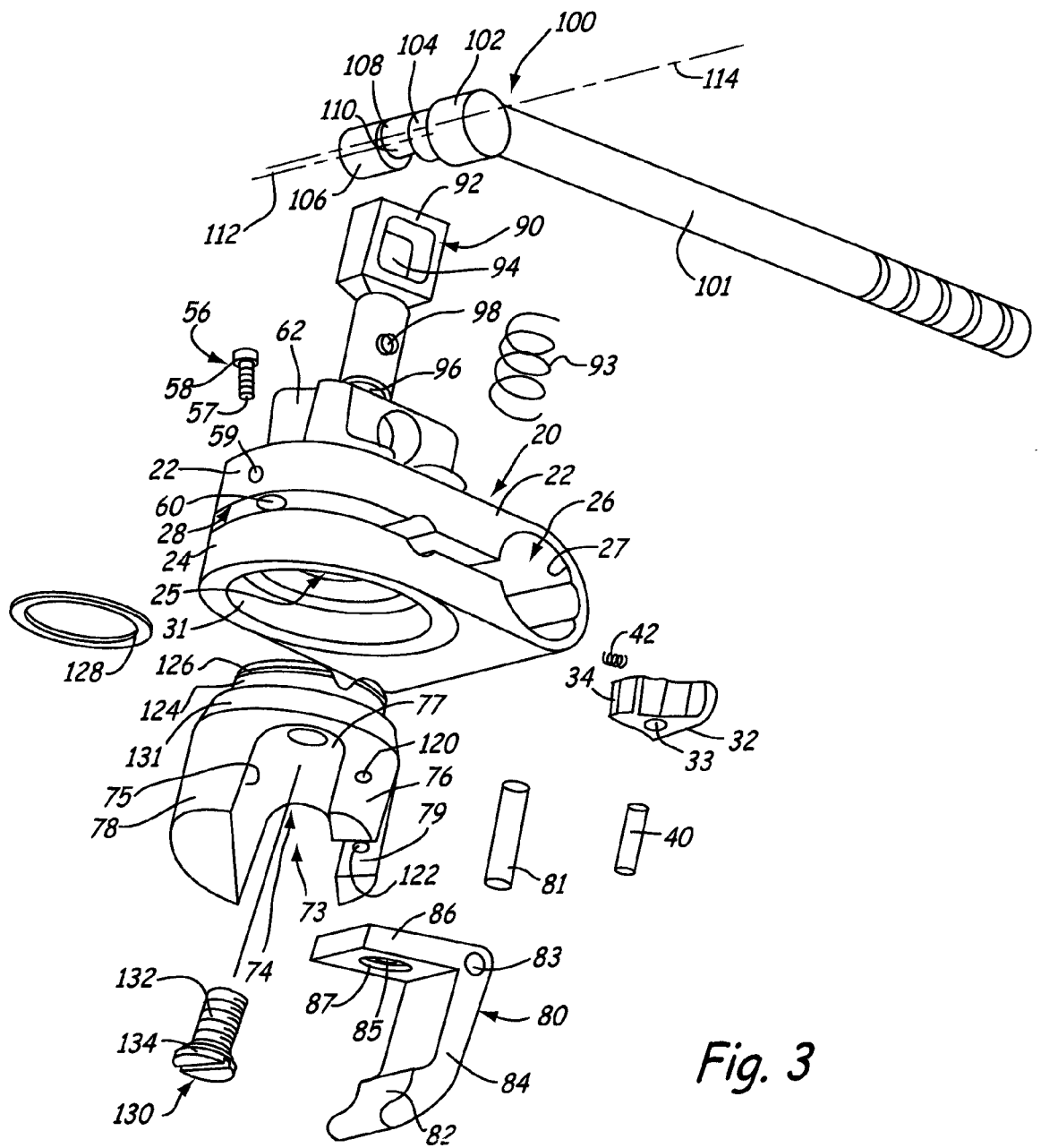
FIG. 3 is an exploded view of the surgical clamp of the present invention.
Figure 11:
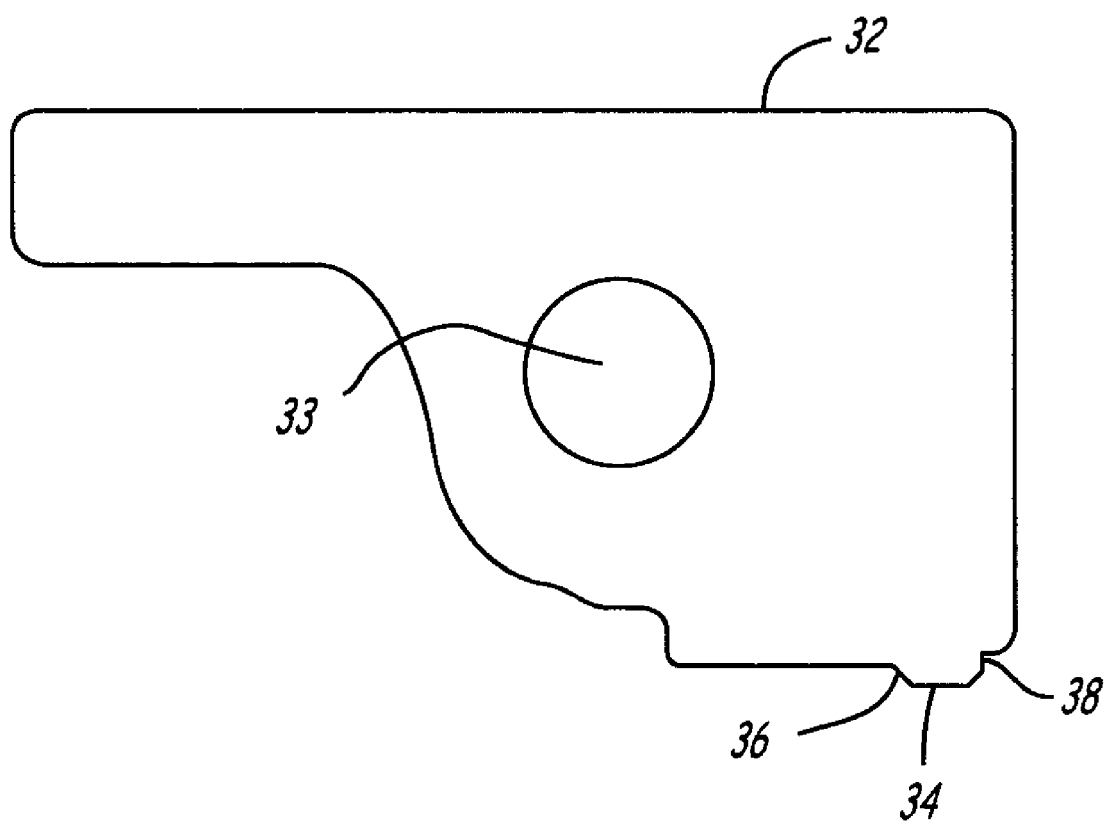
FIG. 11 is a side view of the pawl attached to the first clamping member of the present invention.

A pivot pin 40 is positioned through through holes (33, not shown) in sides of the pawl 32 and through holes (not shown) in sidewalls of the frame 30 to pivotally attach the pawl 32 to the first clamping member 20, as best illustrated in FIGS. 2, 3, and 11. Referring to FIG. 3, a compression spring 42 biases the gripping end 34 of the pawl 32 within the clamping bore 26 and into engagement with the plurality of annular grooves 15.

Referring to FIG. 11, the gripping end 34 of the pawl 32 includes a slanted surface 36 and a substantially right angled surface 38. The slanted surface 36 slides over and does not engage the plurality of annular grooves 15. The right angled surface 36 engages one of the plurality of the annular grooves 15 and retains the first clamping member 20 on the field post 16 while the first clamping member 20 is rotatable about the field post 16.

The design of the pawl 32 allows the first clamping member 20 to freely travel in the direction where the slanted surface engages 36 the plurality of annular grooves 15 and prevents travel in the opposite direction where the substantially right angled surface 38 engages one of the plurality of the annular grooves 15. To move the first clamping member 20 in the opposite direction of the free travel, manual force is applied to the pawl 32 to overcome the bias of the compression spring 42 which removes the gripping end 34 from the clamping bore 26. With the gripping end 34 removed from the clamping bore 26, the first clamping member 20 freely travels along the field post 16 in either direction.

Figure 10:
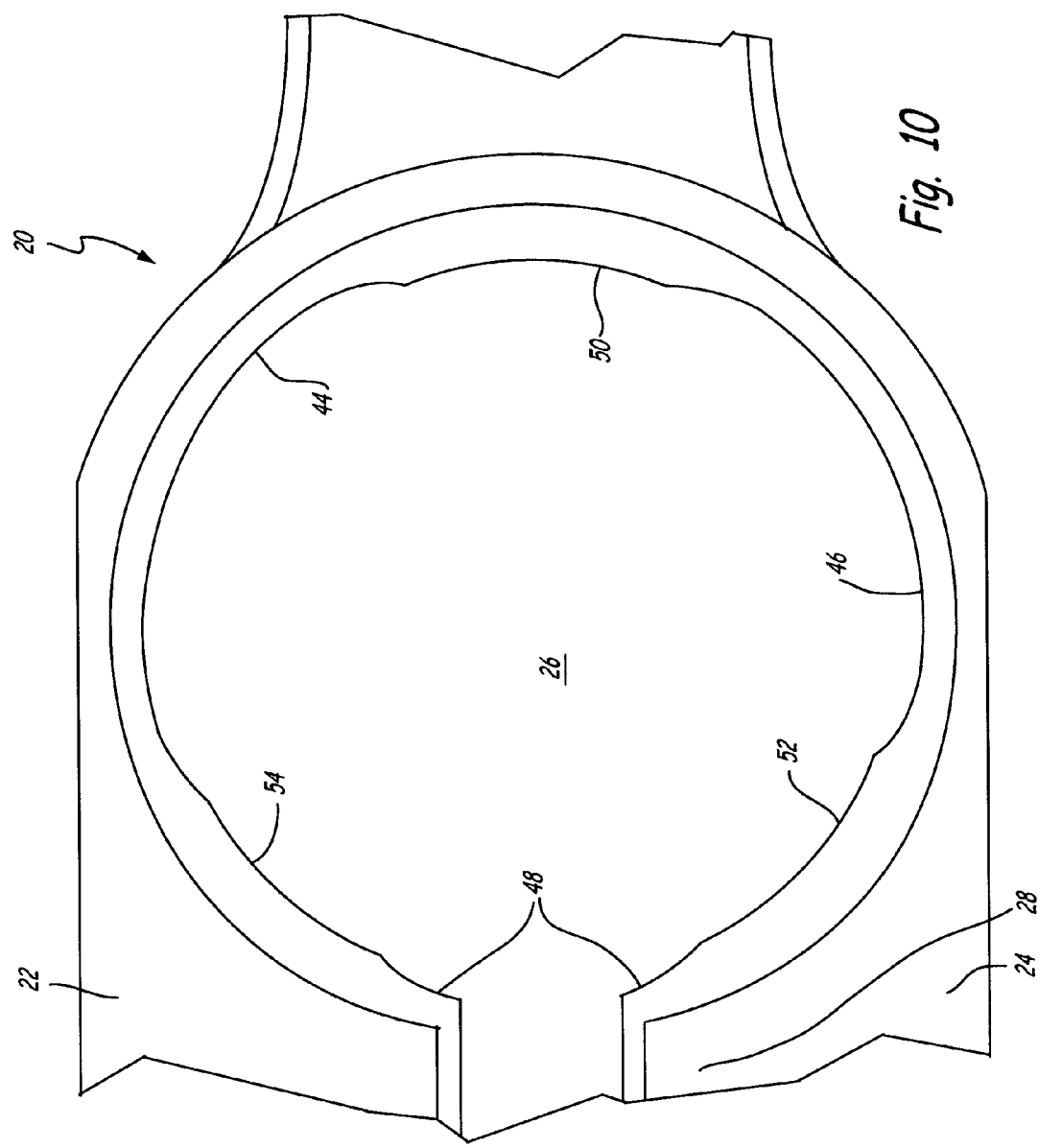
FIG. 10 is a side view of the clamping bore of the first clamping member of the present invention.

Referring to FIGS. 2, 3 and 10, the first clamping member 20 is secured onto the field post 16 by constricting the clamping bore 26 about the field post 16 by forcing the first and second resilient legs 22, 24, respectively, together by positioning the actuating mechanism 100 into the second clamping position. Referring to FIG. 10, the clamping bore 26 is defined by raised arcuate clamping surfaces 50, 52 and 54 which are separated by recessed arcuate surfaces 44, 46 and 48. The recessed arcuate surfaces 44, 46 and 48 are grooves within the clamping bore 26 which make the clamping surfaces 50, 52 and 54, the surfaces that engage the field post 16.

In an exemplary configuration, the raised surface 50 is located opposite the clamping slot 28 and the raised surfaces 52, 54 are located proximate to and separated by the clamping slot 28. A clamping bore having two or more raised surfaces is within the scope of the invention.

As the clamping bore 26 is constricted by a force applied to the shaft 90 by the actuating mechanism 100, the raised surfaces 52, 54, respectively, contact the field post 16 and urge the field post 16 into the raised surface 50. When the first clamping member 20 is in the clamping position, the field post 16 is frictionally engaged along lengths of the raised surfaces 50, 52 and 54.

The clamping strength of the first clamping member 20 having a grooved clamping bore 26 with the raised surfaces 50, 52 and 54 separated by the recessed surfaces or grooves 44, 46 and 48 is significantly greater than that of a smooth surfaced clamping bore. A significant amount of the clamping strength of a smooth bore occurs at two points on a plane having a substantially orthogonal relationship to the clamping slot 28 separating the first and second resilient legs 22, 24, respectively. In comparison to clamping substantially at two points, the first clamping member 20, having the grooved clamping bore 26, engages the field post 16 along the lengths of the raised arcuate surfaces 50, 52, 54 which significantly increases the clamping surface that frictionally engages the field post 16 and thereby increases the clamping strength of the first clamping member 20.

Referring to FIG. 3, a stop 56 is positioned into the clamping slot 28 to prevent an excessive clamping force from being applied to the field post 16 by the first clamping member 20. Excessive clamping force can cause the metal from the field post 16 and/or the first clamping member 20 to wear. The stop 56 is preferably a threaded bolt 58 that threadably engages a threaded bore 60 in the first resilient leg 22 where an end 57 of the bolt 58 is positioned within the clamping slot 28. The bolt 58 is secured into the selected position by deforming the threads through a bore 59 intersecting the threaded bore 60.

Figure 4:
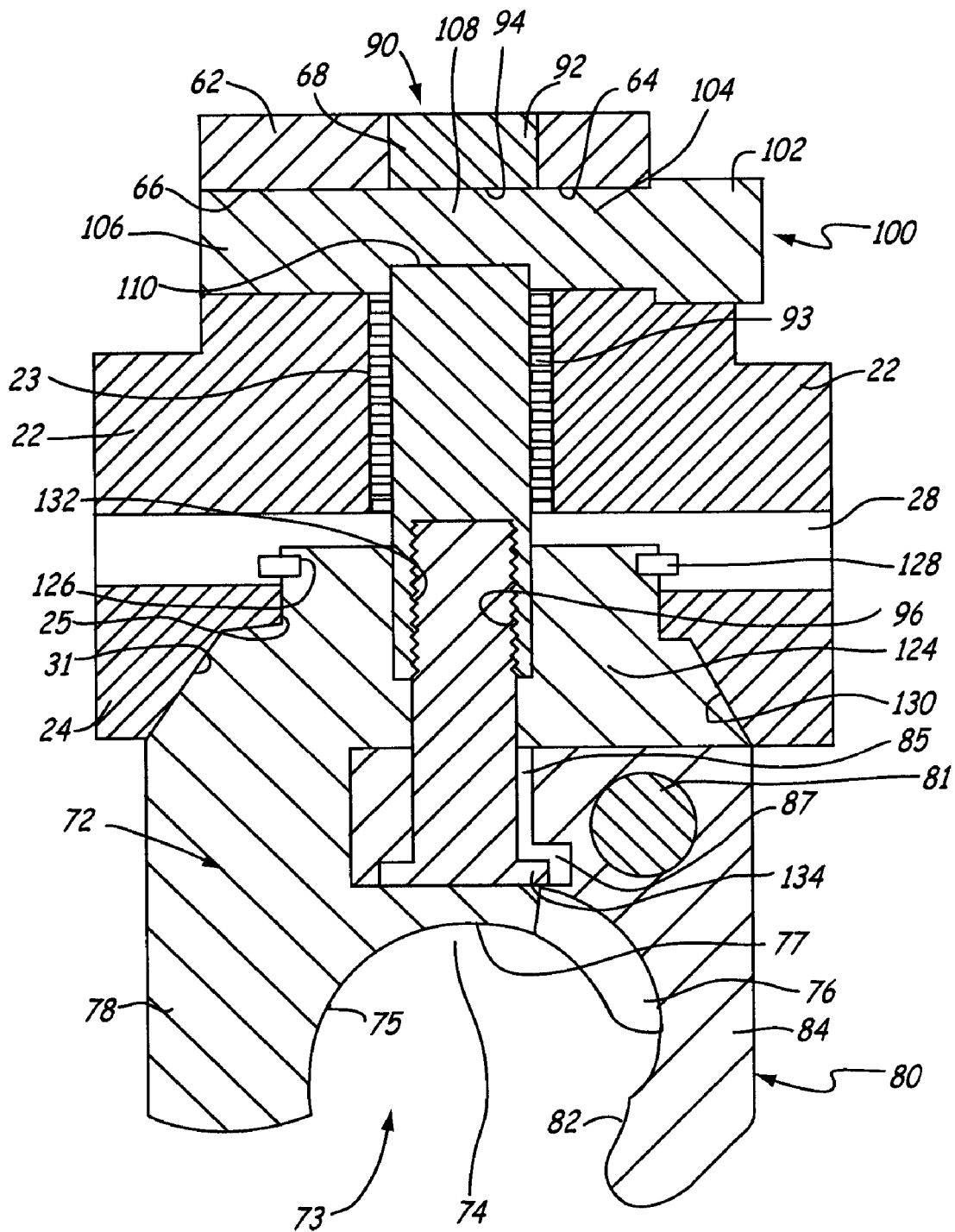
FIG. 4 is a sectional view of the surgical clamp of the present invention in a clamping position along section line 4—4 in FIG. 2.

Referring to FIGS. 3 and 4, the actuating mechanism 100 is preferably a camming pin 102 that is positioned within through bores 64, 66 of a collar 62 such that a camming surface 110 is positioned within a through bore 94 of a head 92 of the shaft 90. The collar 62 is preferably an integral portion of the first resilient leg 22 and includes a shaft head accepting bore 68 that intersects the through bores 64, 66. However, the collar 62 may be a separate component from the first clamping member 20 while being within the scope of the present invention.

The camming pin 102 includes end portions 104, 106 and an intermediate portion 108 having the camming surface 110. The end portions 104, 106 and the intermediate portion 108 are generally cylindrical in shape and are located adjacent one to another. The end portions 104, 106 are centered about a rotational axis 112 and are captivated within the through bores 64, 66, respectively. The captivated end portions 104, 106 rotatably support the intermediate portion 108 within the through bore 94 in the head 92 of the shaft 90.

The shaft 90 is positioned through the shaft head accepting bore 68 which is aligned with first and second shaft passing bores 23, 25 within the first and second resilient legs 22, 24, respectively, until the head 92 is positioned within the shaft head accepting bore 68. The shaft head accepting bore 68 is elongated to allow the required movement of a head 92 of the shaft 90 when the clamp 10 is positioned from the first nonclamping position to the second clamping position and also in the reverse direction as best illustrated in FIG. 2.

Referring to FIGS. 3, and 4, the intermediate portion 108 is eccentrically coupled between the end portions 104, 106. The intermediate portion 108 has an axis 114 that is spaced from the rotational axis 112 of the camming pin 102 by a selected distance. The distance separating the axis 112 of the camming pin 102 and the axis 114 of the intermediate portion 108 generally determines the maximum distance that the camming pin 102 moves the shaft 90 relative to the first and second clamping members 20, 70, respectively. Preferably, the distance separating the axis 112 of the camming pin 102 and the axis 114 of the intermediate portion 108 is sufficient to frictionally secure the field post 16 and the retractor support apparatus 18 within the first and second clamping members 20, 70, respectively.

Other camming mechanisms besides the camming pin 102 described are within the scope of the invention, including, but not limited to, an irregular shaped lobe, a head having increasing radii to an external surface from a pivot point and an eccentric. Other actuating mechanisms 100 besides a camming mechanism are also within the scope of the invention including but not limited to a moving wedge or a threaded rod as described in U.S. Pat. Nos. 4,718,151, 5,020,195 or 5,242,240 herein incorporated by reference.

Referring to FIGS. 2–4, the second clamping member 70 is positioned proximate the second resilient leg 24. The second clamping member 72 includes a main body 72 having a socket 74 that accepts the retractor support apparatus 18. A clamping lever 80 pivotally attached to the main body 72 by a pivot pin 81 includes an arcuate surface 82 on a first leg 84 that constricts an entrance 73 to the socket 74. By socket is meant an opening or a cavity into which an inserted part, such as a retractor support apparatus, is designed to fit and wherein the retractor support apparatus can be inserted into the socket from an infinite number of directions in a 180° range starting from a substantially parallel position to a back surface of the socket to a position substantially perpendicular to the back surface and continuing to position again substantially parallel to the back surface of the socket.

To position the retractor support apparatus 18 within the socket 74, the retractor support apparatus 18 is positioned proximate the entrance 73 to the socket 74 defined by surfaces 75 of first and second walls 76, 78 separated by a back surface 77. Manual force is applied to the retractor support apparatus 18 substantially perpendicularly to an axis 17 to position the retractor support apparatus 18 within the socket 74. However, the retractor support apparatus 18 can be inserted from any position within a substantially 180° range as discussed previously.

The retractor support apparatus 18 is retained within the second clamping member 70 by the arcuate surface 82 of the clamping lever 80 and the surfaces 75 of the first and second walls 76, 78. A compression spring 93 is positioned about the shaft 90 and biases the clamping lever 80 toward a clamping position which retains the retractor support apparatus 18 within the socket 74 as best illustrated in FIGS. 3 and 4. With the retractor support apparatus 18 retained within the socket 74, the retractor apparatus 18 is slidably positionable parallel to the axis 17 within the second clamping member 70.

The clamping lever 80 is positioned within a channel 79 in the first wall 76 and is pivotally attached to the first wall 76 by the pivot pin 81. The pivot pin 81 is positioned through aligned bores 120, 122 intersecting the channel 79 and through bore 83 in the clamping lever 80.

The retractor support apparatus 18 is fixedly retained in a select position by positioning the actuating mechanism 100 into the second clamping position by applying a force to the clamping lever with a bolt 130 disposed through an elongated through bore 85 within a second leg 86 of the clamping lever 80. The bolt 130 includes a threaded end portion 132 that threadably engages an internal threaded bore 96 within the shaft 90.

A head 134 of the bolt 130 is positioned within a countersunk recess 87 about the through bore 85 such that the head 134 of the bolt 130 does not extend into the socket 74. The first and second legs 84, 86 respectively of the clamping lever 80 are generally configured in the shape of the letter "L". When the force is applied to the second leg 96 by the bolt 130, the clamping lever 80 pivots about the pivot pin 81 such that the arcuate surface 82 of the first leg 84 engages the retractor support apparatus 18 as illustrated with dotted lines in FIG. 2.

With the head 134 of the bolt 130 a selected distance from the head 92 of the shaft 90, the first and second clamping members 20, 70, respectively, are positionable between the clamping and non-clamping positions when the actuating mechanism 100 is in the first non-clamping and second clamping positions, respectively. The selected distance between the head 92 of the shaft 90 and the head 134 of the bolt 130 is fixed by inserting a punch into an opening 98 in the shaft 90 and deforming the threads to prevent the bolt 130 from threadably moving out of the threaded bore 96.

The second clamping member 70 is rotatably captivated with respect to the first clamping member 20 by positioning a generally cylindrical end portion 124 within the second shaft passing bore 25 of the second resilient leg 24. An annular groove 126 on the generally cylindrical end portion 134 is positioned within the clamping slot 28 and a snap ring 128 is positioned within the annular groove 126 to captivate the second clamping member 70 with respect to the first clamping member 20.

The second clamping member 70 is rotatably fixed with respect to the first clamping member 20 when the camming pin 102 is positioned into the second clamping position. The head 134 of the bolt 130 forces the second clamping member 70 towards the first clamping member 20 wherein a first frusto-conical surface 131 of the second clamping member 70 frictionally engages a second frusto-conical surface 31 of the second shaft passing bore 25.

In operation, the clamp 10 is typically used to clamp the retractor support apparatus 18 to the field post 16, although the clamp 10 can also be used to clamp a first rod to a second rod. Preferably, the field post 16 includes the plurality of annular grooves 15 uniformly spaced apart.

With the clamp 10 in the first non-clamping position, the first clamping member 20 is slid over the field post 16 in a first direction where the slanted surface 36 of the gripping end 34 of the pawl 32 slides over the plurality of annular grooves 15 thereby allowing the first clamping member 20 to freely move in the first direction. Alternatively, the first clamping member 20 can be moved in an opposite direction by displacing the gripping end 34 from the clamping bore 27 by overcoming the bias of the compression spring 42. When the first clamping member 20 is in a selected position on the field post 16 the substantially right angled surface 38 of the gripping end 34 engages one of the annular grooves 15 such that the first clamping member 20 is rotatably secured in the selected position about the field post 16.

With the first clamping member 20 rotatably secured to the field post 16 by the pawl 32, the retractor support apparatus 18 is positioned proximate the constricted entrance 73 to the socket 74 of the second clamping member 70. Manual force is exerted upon the retractor support apparatus 18 preferably substantially perpendicular to the back surface 77 of the socket 74 (or within a substantially 180° range from the back surface 77) to overcome the bias of the compression spring 93 on the clamping lever 80 to position the retractor support apparatus 18 within the socket 74. The retractor support apparatus 18 is retained within the socket 74 by the arcuate surface 82 of the clamping lever 80 constricting the entrance 73 where the retractor support apparatus 18 is slidably positionable within the socket 74.

The second clamping member 70 is rotatably positioned into a selected position with respect to the first clamping member 20.

With the first clamping member 20 in the selected position on the field post 16 and the retractor support apparatus 18 in a selected position with respect to both the field post 16 and the second clamping member 20, the clamp 10 is positioned into the second clamping position by manipulating a handle 101 attached to the camming pin 102. As the handle 101 is moved, the camming pin 102 is rotated from the first non-clamping position to the second clamping position, and the camming surface 110 of the intermediate portion 108 contacts the through bore 94 within the head 92 of the shaft 90 and generates a force upon the first and second clamping members 20, 70, respectively.

The force applied to the first clamping member 20 causes the first and second resilient legs 22, 24, respectively, to be forced toward each other. As the first and second resilient legs 22, 24 are forced toward each other, the raised arcuate surfaces 50, 52 and 54 of the grooved clamping bore 26 frictionally engage the field post 16.

The force also causes the head 134 of the bolt 130 to be drawn into the counter-sunk recess 87 within the second leg 86 of the clamping lever 80. As the head 134 of the bolt 130 is drawn into the second leg 86, the clamping lever 80 pivots about the pivot pin 81 and causes a frictional engagement between the arcuate surface 82 of the clamping lever 80, the retractor support apparatus 18 and the clamping surface 75 of the second clamping member 70.

The force generated by the camming pin 102 rotatably fixes the second clamping member 70 with respect to the first clamping member 20. The second clamping member 70 is retained in a selected position by the frictional engagement of the frusto-conical surfaces 131, 31 of the second clamping member 70 and the second resilient leg 24, respectively.

To relocate or readjust the retractor support apparatus 18 with respect to the field post 16, the camming pin 102 is positioned from the second clamping position to the first non-clamping position such that the retractor support apparatus 18 is slidably retained within the second clamping member 70. With the camming pin 102 in the first non-clamping position, the second clamping member 70 is rotatable with respect to the first clamping member 20.

The retractor support apparatus 18 is removable from the second clamping member 70 by applying a force preferably substantially perpendicular to the back surface 77 of the socket 74 (or within the substantially 180° range from the back surface 77) in an opposite direction of the force used to position the retractor support apparatus 18 within the socket 74. The force causes the arcuate surface 82 of the clamping lever 80 to pivot away from the entrance 73 to the clamping slot 94 by overcoming the bias of the spring compression 93 such that the entrance 73 is not constricted. With a non-constricted entrance 73, the retractor support apparatus 18 is removable from the second clamping member 70.

Additionally, the location of the first clamp 20 can be adjusted on the field post 16 by either moving the first clamping member 20 in the direction of free travel where the slanted surface 36 of the gripping end 34 of the pawl 32 slides over the annular grooves 15 of the field post 16. Alternatively, to move the first clamping member 20 in the opposite direction, manual force is applied to the pawl 32 to overcome the bias of the compression spring 42 such that the gripping end 34 is positioned away from the clamping bore 26. With the gripping end 34 positioned away from the clamping bore 26, the first clamping member 20 can be positioned along the field post 16 in either direction.

Figure 5:
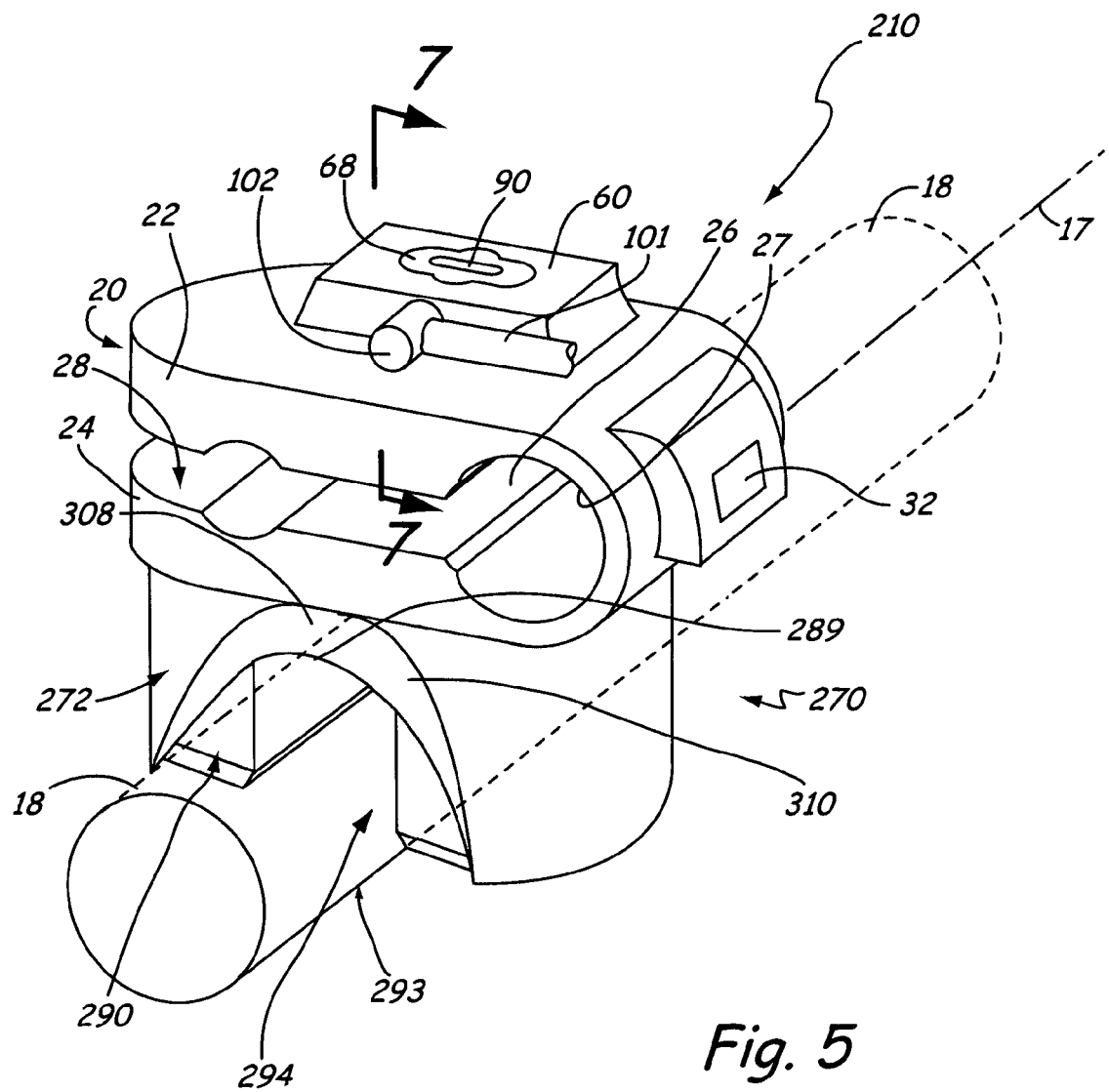
FIG. 5 is a perspective view of an alternative embodiment of the surgical clamp of the present invention.

An alternative embodiment of the clamp of the present invention is generally illustrated at 210 in FIG. 5. The embodiment 210 includes a similar first clamping member 20 and a different second clamping member 270 from the first embodiment 10. In describing the embodiment 210, like reference characters will be used to describe like elements throughout the drawings.

Figure 6:
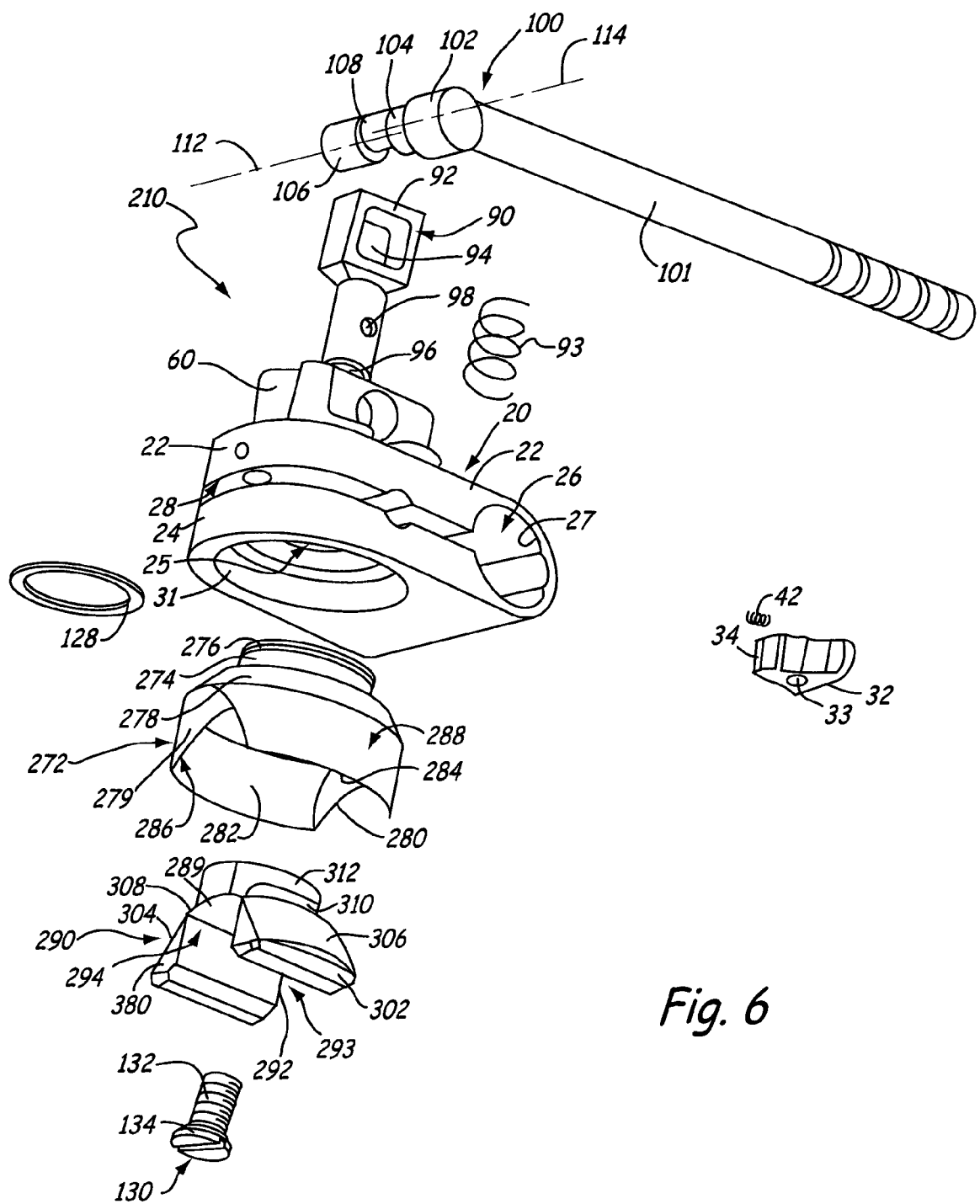
FIG. 6 is an exploded view of the alternative embodiment of the surgical clamp of the present invention.
Figure 7:
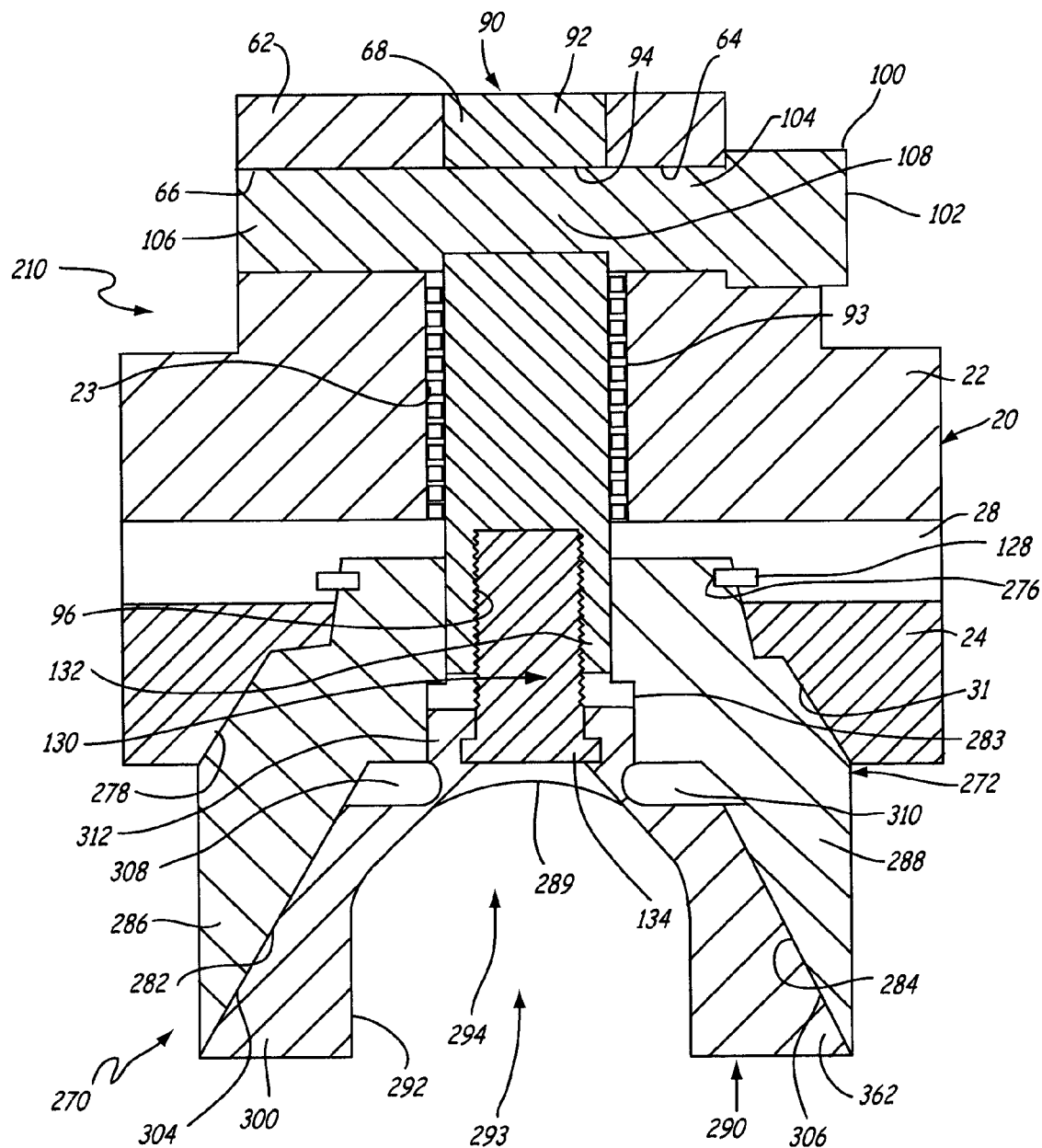
FIG. 7 is a sectional view of the alternative embodiment of the surgical clamp of the present invention in a clamping position along section line 7—7 in FIG. 5.

Referring to FIGS. 5–7, the second clamping member 270 includes a flexing member 290 that slidably cooperates with a spacer 272. The spacer 272 includes a substantially cylindrical end portion 274 that is disposed within the second shaft passing bore 25 of the second resilient leg 24. An annular groove 276 on the cylindrical end portion 274 is positioned within the clamping slot 28 and a snap ring 128 is positioned within the annular groove 276 to rotatably captivate the spacer 272 to the second resilient leg 24.

A retractor support apparatus 18 is positioned at a constricted entrance 293 to a socket 294 defined by a clamping surface 292 of the flexing member 290. The clamping surface 292 of the flexing member 290 is generally aligned with cut out areas 279, 280 of the spacer 270 that allows the retractor support apparatus 18 to be positioned within the socket 294 without interference from the spacer 270. Manual force is applied to the retractor support apparatus 18 preferably substantially perpendicularly to a bottom surface 289 (or within the substantially 180° range from the back surface 289) of the socket 294 to position the retractor support apparatus 18 within the socket 294.

The constricted entrance 293 slidably retains the retractor support apparatus 18 within the socket 294 where the retractor support apparatus 18 is movable along the axis 17. The force exerted by the compression spring 93 upon a bolt 130 disposed through bores in the flexing member 290 and the spacer 270 and threadably engaging the shaft 90 biases the flexing member 290 to make the constricted entrance 293.

The bolt 130 is connected to the shaft 90 by a threadable engagement of a threaded end 132 with the threaded bore 96 within the shaft 90. The bolt 130 is manipulated until a distance from the head 92 of the shaft 90 to the head 134 of the bolt 130 is a selected distance where the first and second clamping members 20, 270, respectively, are positionable between non-clamping and clamping positions when the camming pin 102 is positioned from the first non-clamping position to the second clamping position, respectively. With the bolt 136 in the selected position, the threads of the threaded end 132 are deformed by positioning a punch in the opening 93 in the shaft 90 to fixedly retain the bolt 130 within the shaft 90.

Referring to FIGS. 6 and 7, the second clamping member 270 is positioned into the clamping position when the camming pin 102 is positioned into the second clamping position. The camming pin 102 urges the head 134 of the bolt 130 toward the first clamping member 20 and exerts a force on the flexing member 290 and the spacer 272. The force applied to the spacer 272 creates a frictional engagement between a frusto-conical surface 278 of the spacer 272 with the frusto-conical surface 31 of the second resilient leg 24. The frictional engagement between the frusto-conical surfaces 278, 31 prevents the spacer 272 from rotating with respect to the second resilient leg 24, respectively.

The retractor support apparatus 18 is frictionally engaged by the clamping surface 292 defining the socket 294. The clamping surface 292 is defined by inner surfaces of first and second wings 300, 302, respectively, separated by the arcuate bottom surface 289. As the flexing member 290 is drawn into the spacer 270, arcuate tapered outer surfaces 304, 306 of the first and second wings 300, 302, respectively, slidably engage arcuate tapered inner surfaces 282, 284 of first and second sidewalls 286, 288 of the spacer 270. As the arcuate outer tapered surfaces 304, 306 of the first and second wings 300, 302, respectively, slidably engage the inner arcuate tapered surfaces 282, 284 of the first and seconds sidewalls 286, 288, respectively, first and second cut outs 308, 310 located between the first and second wings 300, 302, respectively, and an end portion 312 flex.

The first and second cut outs 308, 310 flex to conform the arcuate tapered outer surfaces 304, 306 of the first and second wings 300, 302 with an angle of pitch of the arcuate tapered inner surfaces 282, 284 of the first and second sidewalls 286, 288, all respectively. As the arcuate tapered outer surfaces 304, 306 of the first and second wings 300, 302 conform to the arcuate tapered inner surfaces 282, 284 of the first and second sidewalls 286, 288, the socket 294 is constricted. The constricted socket 294 creates the frictional engagement between the clamping surface 292 and the retractor support apparatus 18.

In the non-clamping position an angle of pitch of the arcuate tapered outer surfaces 304, 306 of the first and second wings 300, 302 is shallower than an angle of pitch of the arcuate tapered inner surfaces 282, 284 of first and second sidewalls 286, 288 such that the arcuate tapered outer surfaces 304, 306 do not completely engage the arcuate tapered inner surfaces 282, 284. In the non-clamping position, the retractor support apparatus 18 is slidably positionable within the socket 294.

An end portion 312 of the flexing member 290 is rotatably fixed and slidable within a counter-bored recess 283 positioned about the through bore in the spacer 270. The end portion 312 includes a generally square cross-section that is positioned within the counter-bored recess 283 which also has a generally square cross-section. Flat surfaces of the end portion 312 engage flat surfaces of the counter-bored recess 283 to prevent the flexing member 290 from rotating within the spacer 270.

In operation, the camming pin 102 is positioned into the first non-clamping position where the first clamping member 20 is positionable on the field post 16. The first clamping member 20 is retained in a selected position on the field post 16 by the substantially right angled surface 38 of the pawl 32 engaging one of the annular grooves 15 of the field post 16.

The retractor support apparatus 18 is positioned proximate the constricted entrance 293 to the socket 294 of the second clamping member 270. Manual force is applied substantially perpendicularly to the axis 17 of the retractor support apparatus 18 and preferably substantially perpendicularly to the back surface 289 (or within the substantially 180° range from the back surface 289) of the socket 294 to overcome the constricted entrance 293 created by the bias of the compression spring 93 to position the retractor support apparatus 18 within the socket 294. With the retractor support apparatus 18 positioned within the socket 294, the retractor support apparatus 18 is slidably positioned into a selected position within the socket 294 and rotated into a selected orientation with respect to the field post 16.

With the retractor support apparatus 18 in the selected position, the handle 101 which is fixedly attached to the camming pin 102 is moved to rotate the camming pin 102 from the first non-clamping position to the second clamping position. With the camming pin 102 in the second clamping position, the first clamp 20 frictionally engages the field post 16 as previously described.

As the camming pin 102 is rotated into the second position, the head 134 of the bolt 130 is raised with respect to the second clamping member 270 and pulls the flexing member 290 into the spacer 270. As the flexing member 290 is pulled into the spacer 270, the first and second cut outs 308, 310 flex such that the arcuate tapered outer surfaces 304, 306 of the first and second wings 300, 302 conform to the arcuate tapered inner surfaces 282, 284 of the first and second sidewalls 286, 288, all respectively. As the first and second wings 300, 302 conform to the pitch of the arcuate tapered inner surfaces 282, 284 of the first and second sidewalls 286, 288, the socket 294 constricts and creates a frictional engagement between the clamping surface 292 and the retractor support apparatus 18.

The spacer 270 is forced into the second resilient leg 24 of the first clamping member 20 such that the frusto-conical surface 278 of the spacer 270 frictionally engages the frusto-conical surface 31 of the second resilient leg 24. The frictional engagement of the frusto-conical surfaces 278, 31 prevents the spacer 270 from rotating with respect to the first clamping member 20.

To relocate or readjust the retractor support apparatus 18 with respect to the field post 16, the camming pin 102 is positioned from the second clamping position to the first non-clamping position such that the retractor support apparatus 18 is slidably retained along the axis 17 within the second clamping member 270. With the camming pin 102 in the first non-clamping position, the flexing member 290, having spring characteristics, returns to a non-flexed state and the retractor support apparatus 18 is removable from the second clamping member 270 by applying a force substantially perpendicular to the bottom surface 289 (or within the substantially 180° range from the back surface 289) of the socket 294 and away from the second clamping member 270.

Figure 8:
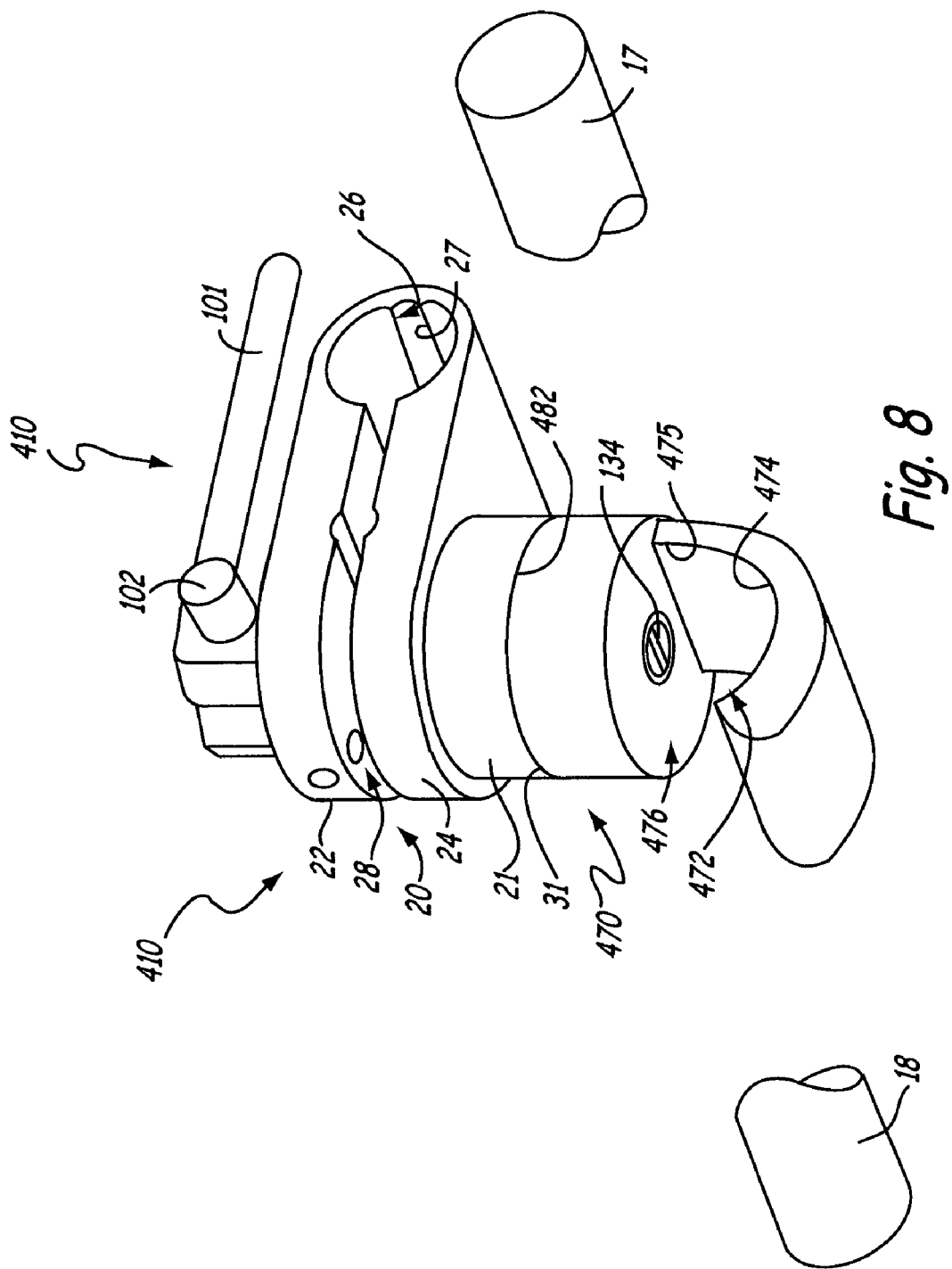
FIG. 8 is a perspective view of another alternative embodiment of the surgical clamp of the present invention.

Another embodiment of the clamp of the present invention is generally illustrated at 410 in FIG. 8. The embodiment 410 includes a substantially similar first clamping member 20 and a different second clamping member 470 from the first embodiment 10 and the first alternative embodiment 210. Like reference characters will be used to describe like elements throughout the drawings.

Figure 9:
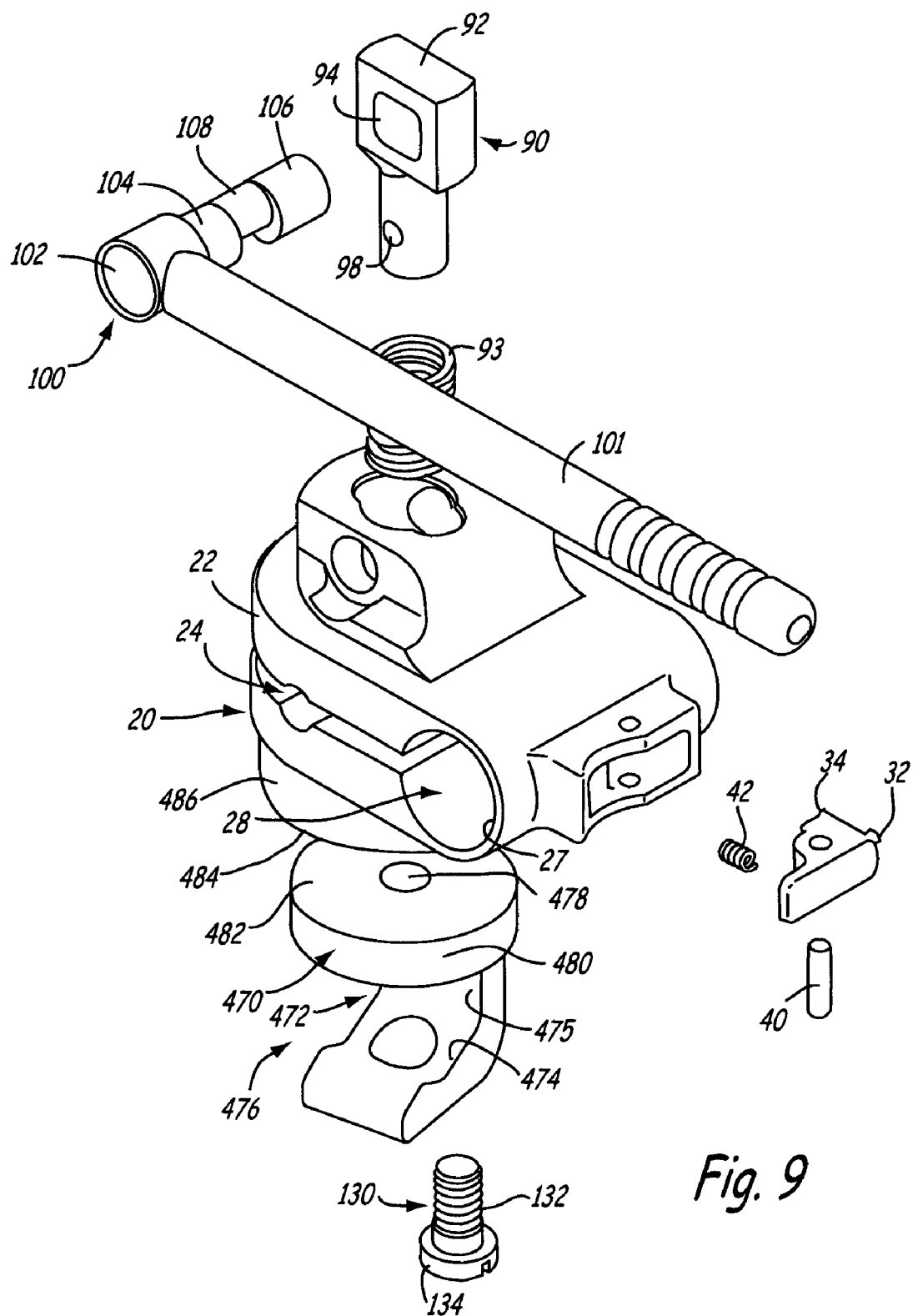
FIG. 9 is an exploded view of the alternative embodiment of the surgical clamp of the present invention.

Referring to FIGS. 8 and 9, the second clamping member 470 comprises a unitary structure having a socket 472 defined by a surface 474 including a back surface 475 for engaging and retaining a retractor support apparatus 18. The retractor support apparatus 18 is positioned proximate a constricted entrance 476 to the socket 472. Manual force is exerted upon the retractor support apparatus 18 substantially perpendicularly to the back surface 475 (or within the substantially 180° range from the back surface 475) of the socket 294. The retractor support apparatus 18 is forced into the socket 472 and retained within the socket 472 by the constricted entrance 476.

The second clamping member 470 is rotatably attached to the first clamping 20 member with a bolt 130 positioned through a through bore 478 within the second clamping member 470 where the bolt 130 threadably engages the threaded internal bore 96 within the shaft 90. With a head 134 of the bolt 130 a selected distance from the head 92 of the shaft 90, a portion of the threads 132 are deformed to retain the bolt 130 within the shaft 90. The head 134 of the bolt 130 is positioned within a counter-bored recess 480 about the through bore 478 such that the head 134 does not interfere with the retractor support apparatus 18 being positioned within the socket 472.

The clamp 410 is positioned into a clamping position where a substantially flat surface 482 of the second clamping member 470 frictionally engages a substantially flat surface 484 of a cylindrical extension 486 extending from the second resilient leg 24. The frictional engagement of the substantially flat surfaces 482, 484 rotatably fixes the position of the second clamping member 470 with respect to the first clamping member 20.

To position the first and second clamping members 20, 470, respectively into the clamping position, the handle 101 which is attached to the camming pin 102 is moved such that the camming pin 102 is rotated from the first non-clamping position to the second clamping position. With the camming pin 102 in the second clamping position, the first clamping member 20 frictionally engages the field post 16 as previously described.

The second clamping 470 is secured in a selected position by forcing the head 134 of the bolt 130 into the second clamping member 470. The force created by the head 134 of the bolt 130 on the second clamping member 470 causes a frictional engagement between the substantially flat surface 482 of the second clamping member 470 and the substantially flat surface 484 of the generally cylindrical extension 486, thereby retaining the second clamping member 470 in the selected position.

To reposition the first clamping member 20 on the field post 16, the camming pin 102 is positioned into the first non-clamping position. Additionally, with the camming pin 102 in the first position, the second clamping member 470 is rotatable with respect to the first clamping member 20.

To remove the retractor support apparatus 18 from the socket 472, manual force is applied to the retractor support apparatus 18 substantially perpendicularly to the back surface 475 (or within the substantially 180° range from the back surface 475) of the socket 472. Manual force overcomes the constricted opening 476 such that the retractor support apparatus 18 is removed from the socket 472.

Although the present invention has been described with reference to preferred embodiments, workers skilled in the art will recognize that changes may be made in form and detail without departing from the spirit and scope of the invention.

What is claimed is:

1. A surgical joint for connecting first and second support members, the surgical joint comprising:
   a first clamping member comprising a clamping bore wherein a first support member is positionable within the clamping bore and comprising a pawl pivotally mounted to the first clamping member and wherein an end of the pawl engages the first support member to retain the first clamping member in a selected position on the first support member when the first clamping member is not frictionally engaging the first support member;
   a second clamping member comprising a socket wherein the socket accepts a portion of a second support member;
   a shaft disposed through the first clamping member and in communication with the second clamping member; and
   an actuating mechanism coupled to the shaft wherein the actuating mechanism is positionable to force the first clamping member to frictionally engage the first support member and the second clamping member to frictionally engage the second support member.

2. The surgical joint of claim 1 wherein the first clamping member further comprises a plurality of portions extending into the clamping bore wherein the plurality of portions are spaced apart and wherein each of the plurality of portions includes an arcuate surface that frictionally engages the first support member.

3. The surgical joint of claim 1 wherein the end of the pawl comprises:
   a first side having a slanted surface; and
   a second surface having a substantially right angled cut out configuration wherein the second surface engages the first support member to retain the first clamping member in the selected position on the first clamping member.

4. The surgical joint of claim 1 wherein the second clamping member further comprises:
   a main body comprising the socket; and
   a clamping arm pivotally attached to the main body wherein the clamping arm comprises a clamping surface wherein the clamping arm is in communication with the shaft such that when the actuating mechanism is positioned to frictionally engage the first support member, the clamping arm pivots such that second support member is frictionally engaged between the clamping surface of the clamping arm and a surface defining the socket.

5. The surgical joint of claim 1 wherein actuating mechanism comprises a camming member.

6. The surgical joint of claim 1 wherein the second clamping member further comprises a flexible clamping member having wing portions with clamping surfaces that define the socket and wherein as the actuating mechanism forces the second clamping member to frictionally engage the second support member, the wing portions flex such that the clamping surfaces engage the second support member.

7. A surgical clamp for mounting on a support member having a plurality of grooves, the surgical clamp comprising:
   a first clamping member comprising first and second legs defining a clamping bore are movable between a clamping and a non-clamping position; and
   a pawl pivotally coupled to an external surface of the first clamping member wherein an end of the pawl cooperates with a plurality of grooves on a support member to retain the first clamping member in a selected position; and
   an actuating mechanism having a shaft positionable to force the first and second legs toward one another and frictionally engage the support member within the clamping bore.

8. The surgical clamp of claim 7 wherein the first clamping member further comprises a slot intersecting the clamping bore wherein the end of the pawl is positioned within the clamping bore through the slot to engage the plurality of grooves.

9. The surgical clamp of claim 7 wherein the first clamping member further comprises a plurality of portions extending into the clamping bore wherein the plurality of portions are spaced apart and have arcuate surfaces extending into the clamping bore wherein when the actuating mechanism forces the first and second legs together the arcuate surfaces of the plurality of portions frictionally engage the support member.

10. The clamp of claim 7 and further comprising a second clamping member rotatably supported about the shaft and positioned proximate the first clamping member wherein the second clamping member includes a socket that accepts a second support member.

11. The surgical clamp of claim 10 wherein the second clamping member further comprises a flexible clamping member having wing portions with clamping surfaces that define the socket and wherein as the actuating mechanism forces the second clamping member to frictionally engage the second support member, the wing portions flex such that the clamping surfaces engage the second support member.

12. The clamp of claim 10 wherein the second clamping member further comprises:
- a main body comprising the socket and a through bore for receiving the shaft; and
- a clamping arm pivotally attached to the main body wherein the clamping arm comprises a clamping surface wherein the clamping arm is in communication with the shaft such that when the actuating mechanism is positioned to frictionally engage the first support member, the clamping arm pivots such that second support member is frictionally engaged between the clamping surface of the clamping arm and the surface defining the socket.

13. The surgical clamp of claim 7 wherein the actuating mechanism comprises a camming member.

* * * * *